United States Patent
Sheehan et al.

(10) Patent No.: US 8,557,722 B2
(45) Date of Patent: Oct. 15, 2013

(54) LOW BASIS WEIGHT WET WIPES WITH A PLEASING HAND

(75) Inventors: Astrid Annette Sheehan, Cincinnati, OH (US); Jonathan Paul Brennan, Cincinnati, OH (US); Philip Andrew Sawin, Liberty Township, OH (US); Terrill Alan Young, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1138 days.

(21) Appl. No.: 11/166,925

(22) Filed: Jun. 23, 2005

(65) Prior Publication Data
US 2006/0154548 A1    Jul. 13, 2006

Related U.S. Application Data

(60) Provisional application No. 60/583,972, filed on Jun. 29, 2004.

(51) Int. Cl.
| | |
|---|---|
| *D04H 1/54* | (2012.01) |
| *D04H 3/10* | (2012.01) |
| *D04H 5/02* | (2012.01) |
| *B32B 5/02* | (2006.01) |

(52) U.S. Cl.
USPC ............. 442/411; 442/59; 442/408; 442/409; 442/415; 442/123

(58) Field of Classification Search
USPC ............ 442/59, 123, 327, 408, 409, 411, 415
See application file for complete search history.

(56) References Cited

U.S. PATENT DOCUMENTS

| | | | | |
|---|---|---|---|---|
| 3,855,046 | A * | 12/1974 | Hansen et al. | 428/198 |
| 4,100,324 | A | 7/1978 | Anderson | |
| 5,043,155 | A | 8/1991 | Puchalski | |
| 5,534,265 | A | 7/1996 | Fowler | |
| 5,648,083 | A | 7/1997 | Blieszner | |
| 6,103,061 | A * | 8/2000 | Anderson et al. | 162/108 |
| 6,361,784 | B1 * | 3/2002 | Brennan et al. | 424/402 |
| 2001/0055609 | A1 | 12/2001 | Shantz | |
| 2005/0008681 | A1 | 1/2005 | Deckner et al. | |
| 2005/0009431 | A1 | 1/2005 | Chamba et al. | |

FOREIGN PATENT DOCUMENTS

| | | |
|---|---|---|
| WO | WO 01/25522 A | 4/2001 |
| WO | WO 02/077041 A | 10/2002 |
| WO | WO 03/050347 A1 | 6/2003 |

OTHER PUBLICATIONS

McCutcheon's, Emulsifiers & Detergents, North American Edition (1997), vol. 1: pp. 280-289.
McCutcheon's, Functional Materials, North American Edition (1997), vol. 2: throughout.
PCT Search Report, mailed Nov. 14, 2005, 2 pages.

* cited by examiner

*Primary Examiner* — Jennifer A Steele
(74) *Attorney, Agent, or Firm* — William E. Gallagher; Amy M. Foust; Richard L. Alexander

(57) ABSTRACT

A nonwoven material suitable for use as a wet wipe substrate is disclosed. The nonwoven material comprises thermoplastic fibers and is provided with a pattern of embossments that join at least a portion of the thermoplastic fibers. When the material is treated with a cleaning lotion to provide a wet wipe, the wet wipe has a wet CD modulus that is greater than about 25 N/m and less than about 80 N/m.

14 Claims, 2 Drawing Sheets

LOW BASIS WEIGHT WET WIPES WITH A PLEASING HAND

CROSS REFERENCE TO RELATED APPLICATION

This application claims the benefit of U.S. Provisional Application No. 60/583,972, filed Jun. 29, 2004.

FIELD OF THE INVENTION

The present invention is related to disposable wiping articles, and more particularly to wet wipes suitable for use as infant wet wipes.

BACKGROUND OF THE INVENTION

Wet cleansing wipes are well known, and are often referred to as wet wipes, towelettes, and the like. Wet wipes include a substrate, such as a nonwoven web, wet with a cleaning lotion. The lotion can be an aqueous lotion, and may include skin conditioning ingredients.

Wet wipes find use at home or away from home, especially as an aid for cleaning children and infants. For example, wipes are often used to clean an infant's skin during a diaper change. As well, wet wipes find use among adults, often in conjunction with the use of incontinence articles. Other uses of wet wipes include general cleaning tasks where soap, cloths, and running water may be unavailable, unsuitable, or inconvenient for a particular task. In almost all instances, wet wipes are provided as folded, stacked, sheets of disposable wipes, each wipe meant for one-time use. Wet wipes are often referred to as disposable wet wipes.

Historically various types of nonwoven webs have been utilized for use as disposable wet wipes. The various types of nonwovens differ in visual and tactile properties, usually due to the particular production process used in their manufacture. In all cases, however, consumers of disposable wipes, particularly those used as baby wipes, demand softness and flexibility in addition to other functional attributes such as protection against soiling a caregiver's hands and cleaning ability. Softness and flexibility can be correlated to certain measurable physical parameters, but perceived softness is often more subjective in nature, and consumers often react to visual and tactile properties in their assessment of wet wipes.

For example, The Procter & Gamble Co. markets PAMPERS® disposable wipes, that use a nonwoven substrate which is manufactured via a spunlace process and embossed with a decorative pattern. The nonwoven web has a dry basis weight of about 58 to 62 gsm. This spunlaced web provides a low elastic modulus (on the order of 30-50 N/m). The combination of low elastic modulus and appropriate fiber choice give these wipes superior inherent softness. These disposable wipes have enjoyed significant commercial success. Wipe substrates having decorative embossments are described in U.S. Pat. No. 6,361,784.

While such decoratively embossed spunlace-produced wet wipes are quite successful in the marketplace, improvements are still needed. For example, substrate materials with a basis weight substantially lower than the 58-62 gsm materials in current use have satisfactory integrity to provide reliable hand protection when used as a wipe substrate. However, consumers may perceive the reduced basis weight materials as too flimsy. Said another way, the hand of such wipe substrates results in a tactile signal to the user that the wipe is weak and may fail with a resulting lack of protection during the cleaning task.

Accordingly, it would be desirable to provide a material, suitable for use as a wet wipe substrate, that combines the visual and tactile aesthetic appeal of embossed high basis weight wet wipes with the improved value of reduced basis weight.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

SUMMARY OF THE INVENTION

Figure 1:
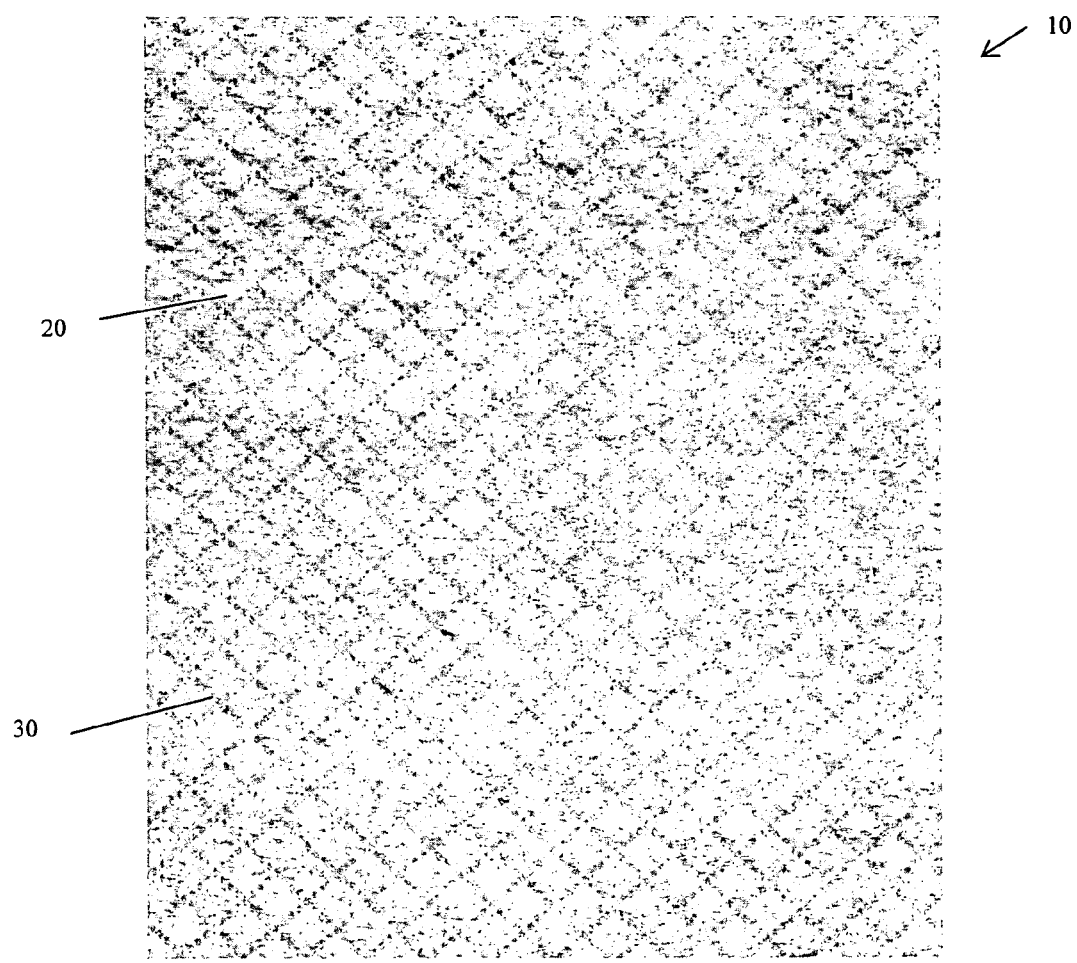
FIG. 1 is a plan view of one emboss pattern of a wipe of the present invention.

A nonwoven material suitable for use as a wet wipe substrate is disclosed. The nonwoven material has a basis weight less than about 55 grams/m$^2$ and comprises thermoplastic fibers. The material is provided with a pattern of embossments that join at least a portion of the thermoplastic fibers. When the material is treated with a cleaning lotion to provide a wet wipe, the wet wipe has a wet CD modulus that is greater than about 25 N/m and less than about 100 N/m and a modulus enhancement ratio greater than about 1.4:1.

DETAILED DESCRIPTION OF THE INVENTION

The wipes of the present invention comprise a nonwoven substrate having a predetermined emboss pattern. The wipe is a wet wipe which is moistened with a cleaning lotion after being embossed. The substrate can comprise a nonwoven web formed of synthetic fibers or combinations of synthetic and natural fibers suitable for use as a wet wipe, and is preferably a soft, flexible nonwoven produced via the spunlace process. The lotion preferably comprises an aqueous emulsion that includes a surfactant and a water soluble/water dispersible organic polymer.

The wipes of the present invention are particularly suitable for dispensing from a tub of stacked, folded wipes, and more preferably for dispensing as "pop-up" wipes, in which upon pulling a wipe out of the tub, an edge of the next wipe is presented for easy dispensing. The wipes of the present invention can be folded in any of various known folding patterns, such as C-folding, but is preferably Z-folded. A Z-folded configuration enables a folded stack of wipes to be interleaved with overlapping portions. Preferred fold patterns are disclosed more fully in commonly assigned, co-pending US Pat. Application 2001/0055609A1.

The term "nonwoven" as used herein refers to a sheet, web, or batt of directionally or randomly oriented fibers, bonded by friction, and/or cohesion and/or adhesion, excluding paper, tissue paper, and products which are woven, knitted, tufted, or stitch-bonded. A web is considered to be a paper web, and therefore categorically not included as a web of the present invention, if the majority of the constituent fibers have a length to diameter ratio less than 300, or a nominal (or average) fiber length of less than about 1 mm. Such relatively short fibers are suitable as a constituent of a fiber blend when the web further comprises long thermoplastic fibers suitable for providing interfiber bonding.

The term "wet wipe" as used herein refers to a wipe which includes a substrate which is moistened, such as by wetting the substrate with a liquid composition, prior to use by the consumer. In particular, "wet wipe" refers to wipes having a substrate which is moistened prior to packaging, such as in a generally moisture impervious container or wrapper. Wet wipes, which can also be referred to as "pre-moistened wipes" and "towelettes", are suitable for use in cleaning infants, and can also find use in cleaning tasks related to persons of all ages. Such wipes can also include articles used for application/removal of substances to/from the body, including but not limited to application of make-up, skin conditioners, ointments, sun-screens, insect repellents, and medications.

As used herein, when used in relation to material compositions the terms "%", "percent", "weight percent" or "percent by weight" refer to the quantity by weight of a component as a percentage of the total, unless indicated otherwise.

As used herein, the term "basis weight" means the weight per unit area of the wipe, or the wipe substrate. One method of determining basis weight, therefore, is to weigh a known area sample that is representative of the material. The units of basis weight are typically expressed as grams per square meter ($g/m^2$).

As used herein, the term "surfactant" refers to materials which preferably orient toward an interface, classes of surfactants including nonionic surfactants, anionic surfactants, cationic surfactants, amphoteric surfactants, zwitterionic surfactants, and mixtures thereof.

As used herein, the terms "emulsifier" or "solubilizer" refer to a component that reduces the tendency of one or more other components in an emulsion used to prepare a lotion composition to phase separate therefrom.

As used herein, with respect to nonwoven webs, the term "machine-direction" or "MD" refers to the direction of web travel as the nonwoven web is produced, for example on commercial nonwoven making equipment. Likewise, the term "cross-direction" or "CD" refers to the direction in the plane of the web perpendicular to the machine-direction. With respect to individual wipes, the terms refer to the corresponding directions of the wipe with respect to the web used to produce the wipe. These directions are carefully distinguished herein because the mechanical properties of nonwoven webs can differ, depending on how the test sample is oriented during testing. For example, tensile properties of a nonwoven web differ between the machine-direction and the cross-direction, due to the orientation of the constituent fibers, and other process-related factors.

For disposable wet wipes suitable for use as a baby wipe, it has been found that softness, flexibility and thickness of the wipe all contribute to consumer satisfaction. It has been found that these consumer-preferred attributes are significantly impacted by the method of making the nonwoven substrate, and the presence or absence of aesthetically pleasing embossed designs. In an effort to quantify, measure, and design in preferred softness and flexibility parameters in a wet wipe, extensive consumer panel testing has been performed. The results of the consumer panel testing revealed that, for a given thickness of the wipe itself, the cross-direction (CD) mechanical property of elastic modulus is a relevant technical measure of consumer-acceptable softness and flexibility. Beyond simply being technically soft and flexible, however, an additional requirement for commercially successful baby wipes is the presence of aesthetically-pleasing embossed designs that can signal added softness and quality to consumers.

Substrate:

The wipe 10 of the present invention as shown in FIG. 1 can comprise a substrate comprising a nonwoven web of synthetic fibers or mixtures of natural and synthetic fibers. Suitable natural fibers include but are not limited to cellulosic fibers, such as wood pulp fibers, cotton, and rayon. Suitable synthetic fibers include fibers commonly used in textiles, including but not limited to polyolefins, such as polypropylene fibers, and other thermoplastic fibers, such as polyester fibers. In a preferred embodiment viscose fibers (rayon made from viscose (cellulose xanthate)) are used in combination with polypropylene for an economical balance of softness and bondability (with respect to embossing). The viscose provides excellent softness and clothlike properties, but used alone tends to produce a flannel-like web, which is not currently preferred by consumers of baby wipes. Polypropylene permits the web to be bonded in an embossing step, but used alone produces a web that some consumers of baby wipes identify as being slick and synthetic-feeling. Blending the two types of fibers changes the flannel-like feel of the viscose fibers into a more silky-feel, which gives the wipes a silky-soft feel, which is consumer approved for baby wipes.

Suitably, a substrate of the present invention comprises at least about 5% of a thermoplastic fiber, preferably at least about 10%. If the substrate comprises entirely thermoplastic fiber it should be further processed, to overcome the slick/synthetic feel discussed above.

At least a portion of the fibers must have a surface energy that is high enough to allow them to be readily wet by the cleaning lotion during the wetting step of the wipe manufacturing process. As noted above viscose fibers are a preferred component of fiber blends useful for the wet wipes of the present invention. Such fibers also provide desirable wettability for most cleaning lotions when they are used as a component of a substrate material. Without being bound by theory it is believed that this wettability derives from the relatively high surface energy of viscose rayon (~50 dynes/cm) which is substantially more wettable than polypropylene fibers (surface energy ~35 dynes/cm).

Beyond the particular fiber composition of the nonwoven web, for consumer-preferred, soft, flexible baby wipes, wet CD modulus has been identified as a useful technical measure of desirable "hand". As is known, consumer perception of the hand of a woven or nonwoven textile depends on many factors. One of those factors is the force required to crumple the fabric. It has been found that CD modulus is a useful measure of this force. Since wet wipes are, by definition, saturated with liquid when they are used, a particularly useful measure of hand for a wet wipe is wet CD modulus. A method is disclosed in the Test Methods section below. Currently preferred substrates have a wet CD modulus values of less than about 100 N/m, preferably less than about 90 N/m, more preferably less than about 80 N/m, and particularly preferably less than about 70 N/m. On the other hand, wet CD modus can also be too low. In this instance, users of wet wipes report that they are flimsy and lacking substance. Suitably, a substrate according to the present invention has a wet CD modulus greater than about 25 N/m, preferably greater than about 27 N/m, more preferably greater than about 30 N/m.

Currently, one preferred process for producing soft, flexible, "drapy" webs having desirable CD modulus characteristics is spunlacing. Spunlacing technology is a known method useful in the production of nonwoven webs, and involves laying down a matrix of fibers, for example as a carded or spunbonded web, and entangling the fibers to form a coherent web. Entangling is typically accomplished by impinging the matrix of fibers with high pressure water from a plurality of suitably-placed water jets, often referred to as hydroentangling. In theory, other fluids can be used as the impinging medium, such as compressed air. The fibers of the web are thus entangled, but not physically bonded one to another. The fibers of a spunlaced web, therefore, have more freedom of movement than fibers of webs formed by thermal or chemical bonding. Particularly when lubricated by wetting as a wet wipe, such spunlaced webs provide webs having desirable moduli. Preferred for purposes of the present invention is a spunlaced web formed from an airlaid or carded web comprised of fibers having a predetermined nominal (or average) fiber length of from about 1.9 cm to about 7.6 cm the original bending torque and modulus properties of the precursor web can be substantially preserved. Fiber lengths are predetermined, and supplied by the fiber maker as staple fibers in nominal lengths, which can be specified as average lengths. Typical fiber lengths for carded webs are nominally 30 mm and 50 mm.

Suitably, fibers for use in substrates of the present invention are less than 5 denier, preferably less than 3 denier. Particularly preferred fibers are between about 1.2 denier and 2.2 denier.

The substrate nonwoven may also have a layered structure whereby fibers having a less desirable feel are disposed between layers of fibers having a more pleasing texture. Such structures are described, for example in published PCT Application No. WO 03/050347A1. As will be recognized, for application in the present invention, each of the layers must have enough thermoplastic fiber so that the embossments can join at least a portion thereof.

Also suitable are, spunbond webs and layered webs (e.g., spunbond/meltblown/spunbond webs where the meltblown fibers, although discontinuous, are melt-bonded to adjacent fibers, which may result in a relatively somewhat stiffer web compared to other nonwoven materials are sandwiched between two softer spunbonded layers). Additional processing may be required to modify the surface texture of substrates that comprise substantially only thermoplastic polymers to eliminate the slick/synthetic feel discussed above.

An additional suitable web material for the present invention are those webs comprising an air-formed matrix of thermoplastic polymer microfibers having an average fiber diameter of less than about 10 microns, and a multiplicity of individualized wood pulp fibers disposed throughout the matrix of microfibers and engaging at least some of the microfibers to space the microfibers apart from each other as are described in U.S. Pat. No. 4,100,324.

The constituent fibers of the web of the present invention can be circular in cross-section, dog bone shaped, delta (i.e., triangular cross-section), tri-lobal, ribbon, or other shapes as may be known as suitable for production of nonwoven materials. Likewise, the fibers can be conjugate fibers, such as bicomponent fibers. Staple fibers may be crimped, and may have a finish, such as a lubricant, applied.

For use as a wet wipe, webs of the present invention have a dry basis weight of less than about 55 grams per square meter (gsm) in order to provide desirable increased value to a user. Suitably, the basis weight is greater than about 35 gsm. Typically, the basis weight is between about 40 gsm and about 55 gsm. Preferably, the basis weight is less than about 53 gsm. A particularly preferred embodiment has a basis weight between about 47 gsm and 52 gsm.

It will be recognized that, as basis weight decreases, the number of fiber intersections available for entanglement goes down. Thus, unless proper precautions are taken webs having low basis weight (desirable for production of low cost wet wipes) may be perceived as too flimsy. It has been found that substrates according to the present invention, having the combination of wet CD modulus and basis weight described above, provide a particularly desirable combination of good value and desirable hand. For example, a substrate embossed according to the present invention having a basis weight of about 50 gsm has a wet CD modulus that is comparable to the wet CD modulus of a prior art substrate having a basis weight of about 58 gsm that was decoratively embossed in a manner similar to that described in U.S. Pat. No. 6,361,784.

Without being bound by theory, it is believed that increasing bond area as basis weight decreases will increase stiffness by preventing fibers from moving relative to each other. For example, when a fabric is crumpled, the stress applied either strains the fibers or is relieved by fiber motion relative to each other. As will be recognized, the more fibers are prevented from relative motion with respect to each other, the more of an applied stress is directed to fiber straining and the stiffer the fabric feels. Bond area is one measure of fiber movement inhibition. Suitable emboss patterns for the present invention provide a relatively high bond area for a soft/drapable material. Suitably, the emboss pattern provides a bond area greater than about 12% and less than about 25%, preferably greater than about 15% and less than about 25% and more preferably greater than about 15% and less than about 22%. A method for bond area is provided in the Test Methods section below.

Said another way, it is believed that, for a given basis weight, the increased bond area of the emboss patterns of the present invention provides an unexpectedly large modulus increase when compared to the increase in bond area. Referring to Example 1, for example, the decorative emboss pattern of the prior art (~6% bond area) provides an increase in CD modulus of about 10% compared to an unembossed substrate. While a diamond emboss pattern according to the present invention (~20% bond area) provides a 70% to 80% increase in CD modulus compared to an unembossed substrate. Suitably, the CD modulus enhancement ratio, (i.e., the ratio of CD modulus of an embossed substrate to the CD modulus of an unembossed substrate of the same basis weight and fiber configuration (i.e., composition and relative fiber arrangement)) is greater than about 1.4:1, preferably greater than about 1.5:1, more preferably greater than about 1.6:1.

Suitably, the emboss pattern comprises a multitude of regular geometric figures formed by an assembly of embossments. Exemplary figures include, but are not limited to, squares, rhomboids, diamonds, circles, ellipses, polygons and other similar figures. Preferably, where possible, such geometric figures are disposed on the substrate at a predefined angle to the machine direction so as to control the CD bending behavior of the substrate. Suitably this angle can vary between about 30 degrees and about 60 degrees. FIG. 1 shows a wet wipe 10 embossed with a particularly preferred emboss pattern 20 wherein the embossments 30 are disposed in a series of parallel lines at an angle of about ±45 degrees relative to the machine direction so as to form a repeating pattern of diamonds.

It should be noted that the shape of any emboss pattern is independent of the shape of an individual embossment. Such individual embossments which, in assembly, form an emboss pattern also have a predetermined shape. Such predetermined shapes include but are not limited to ovals, squares, rectangles, diamonds, triangles and other geometric figures as may be desired. The area of an individual embossment may also vary. Embossment areas may be less than about 5 mm$^2$, preferably less than about 3 mm$^2$. Suitably the embossment area is greater than about 0.5 mm$^2$, preferably greater than about 1 mm$^2$. A particularly preferred embossment area is between about 1 and 1.5 mm$^2$.

One method of providing an emboss pattern is via known calender-embossing. In a calender-embossing process the nonwoven web is fed into the nip of two counter-rotating calender rolls where at least one of the rolls comprises raised areas that compress and melt-bond adjacent fibers of the nonwoven web in the compressed regions. In many cases one of the rolls is also heated to facilitate the melt bonding.

A particularly preferred web of the present invention is a spunlaced, carded nonwoven material comprising about 60% polypropylene fibers and about 40% viscose rayon fibers and having a basis weight of about 50 gsm that has been calender embossed using the pattern shown in FIG. 1. Such a material is available from Sandler AG of Schwarzenbach/Salle, Germany as SAWATEX 2642-50.

When wetted, the web of the present invention has excellent softness and flexibility. For example, the spunlaced web of the invention that is described in Example 1 has a wet CD modulus of about 34-38 N/m, depending on the particular cleaning lotion used with the substrate. For comparison purposes, a prior art wet wipe having a basis weight on the order of 58 gsm lotioned with comparable cleaning lotions and decoratively embossed was found to have a wet CD modulus of about 40 N/m.

Cleaning Lotion:

The wet wipe of the present invention comprises an aqueous emulsion, also known as a cleaning lotion. The cleaning lotion is preferably at least about 85 percent by weight water, more preferably at least about 90 percent by weight water, and still more preferably at least about 95 percent by weight water. A currently preferred cleaning lotion is an oil-in-water comprising an emulsifier and an emollient.

Particularly preferred emulsifiers are nonionic surfactants. Examples of nonionic surfactants are disclosed in McCutcheon's, Detergents and Emulsifiers, North American Edition (1997) and McCutcheon's, Functional Materials, North American Edition (1997) both published by Mc Publishing Co. of Glen Rock, N.J.

Nonionic surfactants useful herein include those selected from the group consisting of alkyl glycosides and alkyl polyglycosides. These can be broadly defined as condensation products of long chain alcohols, e.g. $C_{8-30}$ alcohols, with sugars or starches or sugar or starch polymers, i.e., glycosides or polyglycosides. These compounds can be represented by the formula $(S)_n$—O—R wherein S is a sugar moiety such as sorbose, glucose, fructose, mannose, and galactose; n is an integer of from about 1 to about 1000, and R is a $C_{8-30}$ alkyl group. Non-limiting examples of alkyl glycosides and alkyl polyglycosides including polysorbate-20 and polysorbate-60.

Also useful are ethoxylated and propoxylated alcohol ethers and ethoxylated and propoxylated esters and ethoxylated and propoxylated amides. These can be broadly defined as condensation products of long chain alcohols or carboxylic acids or amide, e.g., $C_{8-30}$ alcohols or $C_{8-30}$ carboxylic acids or $C_{8-30}$ carboxylic acid amides, with ethylene oxide and/or propylene oxide.

Also useful are silicone co-polyol surfactants. These can be broadly defined as condensation products of long chain alcohols or carboxylic acids, e.g., $C_{8-30}$ alcohols or $C_{8-30}$ carboxylic acids, with ethylene oxide and/or propylene oxide that are further reacted with poly-dimethylsiloxane. These materials can adopt a number of structures, including but not limited to linear structures, and pendant structures. A non-limiting example is Bis-PEG/PPG-16/16 PEG/PPG-16/16 Dimethicone.

Also useful are ethoxylated and propoxylated mono-, di-, and tri-glycerides. These can be broadly defined as condensation products of long-chain carboxylic acids (e.g., $C_{8-30}$ carboxylic acids) with glycerin where either one or two or three carboxylic acid moieties are bound to the glycerin moiety. Non-limiting examples include PEG-40 hydrogenated castor oil from BASF of Ludwigshafen, Germany as Cremophor C-40, PEG-6 Caprylic/Capric Glycerides from Sasol Germany GmbH of Witten, Germany as Softigen-767 and the glyceryl stearate blends available from Degussa Care Specialties of Hopewell, Va. under the name TEGO CARE.

Also useful are ionic surfactants including anionic surfactants, cationic surfactants and zwitterionic surfactants.

Particularly suited for the present invention are emulsifiers such as alkylpolylglycosides (e.g., Polysorbate 20 available from Uniqema of New Castle, Del.) and a mixture of Caprylic Capric triglyceride and Bis-PEG/PPG-16/16 PEG/PPG-16/16 Dimethicone (ABILCARE 85 from Degussa Care Specialties of Hopewell, Va.) and combinations thereof.

The emulsifier is employed in an amount effective to emulsify the emollient and other non-water-soluble oils that may be present in the composition with enough surface active material still available to facilitate the cleaning task. The cleaning lotion preferably comprises less than about 3 percent by weight of the nonionic surfactant. More preferably, the lotion can comprise less than about 1 percent by weight of the nonionic surfactant. Even more preferably, the lotion comprises between about 0.3 and about 0.6 percent by weight of the nonionic surfactant.

The lotion may also comprise one or more of the following: an effective amount of a rheology modifier; an effective amount of an emollient; effective amount of a preservative, an effective amount of a humectant, and an effective amount of a fragrance.

Rheology modifiers are compounds that increase the viscosity of the composition at lower temperatures as well as at process temperatures. Rheology modifiers or suspending agents or stabilizers also provide "structure" to the compositions to prevent settling out (separation) of insoluble and partially soluble components and/or creaming of the emulsion. Other components or additives of the compositions may affect the temperature viscosity/rheology of the compositions. Particularly suited for the present invention are rheology modifiers such as: carboxylic acid polymers (e.g., Carbopol® 954 from Noveon, Inc. of Cleveland, Ohio), polysaccharides (e.g., cellulose derivatives such as hydroxyethylcellulose as is available from Hercules, Inc. of Wilmington, Del. as Natrosol® CS Plus) and naturally occurring polymers (e.g., carrageenan, gelatin, sodium carboxymethyl dextran, sodium carrageenan, tragacanth gum and xanthan gum). A particularly preferred rheology modifier is a xanthan gum available as KELTROL as is available from CP Kelco U.S. of Wilmington, Del.

As used herein, an emollient is a material that softens, soothes, supples, coats, lubricates, or moisturizes the skin. The term emollient includes, but is not limited to, conventional lipid materials (e.g., fats, waxes), polar lipids (lipids that have been hydrophylically modified to render them more water soluble), silicones, hydrocarbons, and other solvent materials. Emollients useful in the present invention can be petroleum based, fatty acid ester type, alkyl ethoxylate type, fatty acid ester ethoxylates, fatty alcohol type, polysiloxane type, mucopolysaccharides, or mixtures thereof. In one embodiment of the present invention, preferred emollients are silicon based. Silicone-based emollients are organo-silicone based polymers with repeating siloxane (Si—O) units. Silicone-based emollients of the present invention are hydrophobic and exist in a wide range of possible molecular weights. They include linear, cyclic and cross-linked varieties. Silicone oils are generally chemically inert and usually have a high flash point. Due to their low surface tension, silicone oils are easily spreadable and have high surface activity. Examples of silicon oil for the present invention include: Cyclomethicones, Dimethicones, Dimethicone copolyols, phenyl-modified silicones, alkyl-modified silicones, and silicone resins. Other emollients useful in the present invention can be unsaturated esters or fatty esters. An example of an unsaturated ester or fatty ester of the present invention is a caprylic capric triglyceride alone or in combination with bis-PEG/PPG-16/16 PEG/PPG-16/16 Dimethicone.

Humectants are hygroscopic materials that function to draw water into the stratum corneum to hydrate the skin. The water may come from the dermis or from the atmosphere. Examples of humectants include glycerin, propylene glycol, and phospholipids.

Fragrance components, such as perfumes, include, but are not limited to water insoluble oils, including essential oils.

Preservatives prevent the growth of micro-organisms in the liquid lotion and/or on the substrate. Generally, such preservatives are hydrophobic or hydrophilic organic molecules. Suitable preservatives include, but are not limited to parabens, such as methyl parabens, propyl parabens, alkyl glycinates, iodine derivatives and combinations thereof.

Low lotion surface tension is also desirable for cleaning lotions of the present invention so as to facilitate dispersion and removal of soils during a cleaning task. Suitably, the lotion has a surface tension less than about 40 dynes/cm, preferably less than about 37 dynes/cm. A particularly preferred cleaning lotion formulation is disclosed in U.S. patent application Ser. No. 10/883,314, filed on Jul. 1, 2004 in the name of Deckner, et al. A preferred method of producing such cleaning lotions is dilution of a concentrated composition as is described in U.S. patent application Ser. No. 10/883,339, filed on Jul. 1, 2004 in the name of Chamba, et al.

U.S. Pat. Nos. 5,534,265; 5,043,155 and 5,648,083 disclose additional cleaning lotion ingredients.

The wet wipe is made by wetting the dry substrate with at least 1 gram of liquid cleaning lotion per gram of dry fibrous web. Preferably, the dry substrate is wetted with at least about 2.0 gram, and more preferably at least about 2.5 gram, still more preferably at least about 3.0 gram and in one embodiment about 3.4 gram of liquid lotion was added per gram of the dry fibrous web. Suitable methods of delivering the cleaning lotion to the substrate include but are not limited to submersion, spraying, padding, extrusion coating and dip coating. Particularly preferred for commercial production is extrusion coating where the cleaning lotion is applied to a moving web of substrate at the desired add-on rate from an extrusion header (similar to a slot coater). After wetting, the substrate may be folded, stacked, cut to length and packaged as may be desired.

Wet wipes are generally of sufficient dimension to allow for a convenient handling while being small enough to be easily disposed to the sewage system. Typically, the substrate is cut and/or folded to such dimensions as part of the manufacturing process. In some instances the substrate is cut into individual portions so as to provide separate wipes which are often stacked and interleaved in consumer packaging. In other embodiments the wipes are in a web form there the web has been slit and folded to a predetermined width and provided with means (e.g., perforations) to allow individual wipes to be separated from the web by a user. Suitably a wet wipe according to the present invention should have a length between about 100 mm and about 250 mm and a width between about 140 mm and about 250 mm. Preferred dimensions for a wipe as it is typically used are 200 mm long×180 mm wide.

Test Methods
Modulus and Peak Tensile Strength
Scope

This method is suitable for any nonwoven wipe substrate (dry) or finished product (wet) that can be cut to a sample width of 50 mm and References This method applies to any nonwoven wipe material (dry substrate or saturated wet wipes) and is generally based on EDANA 20.2-89. Wipe-specific clarification is provided where the EDANA method is vague or unclear in its application to a wipe product.

Apparatus

| | |
|---|---|
| Cutter | Precision sample cutter capable of cutting a 50 mm wide strip (±0.5 mm). A suitable cutter is manufactured by Thwing-Albert of Philadelphia, PA as the JDC-50M-12. If no precision cutter is available, either 1) a template and scalpel (or similar very sharp knife) may be used, or 2) a die and press may be used. |
| Tensile Tester | Constant Rate of Elongation Tensile Tester, capable of performing the test described herein. A suitable instrument is available from MTS of Cary, NC as the MTS Synergie 200/L and the MTS Alliance RT/1. |
| Software | Software suitable for machine control, data acquisition and data analysis, given a specific tensile tester. TestWorks ® version 4.08 from MTS is suitable for either of the instruments listed above. |
| Load Cell | The load cell should be chosen such that the measured peak force is within the dynamic range of the load cell. |
| Grip faces | 75 mm wide grips recommended. |

Scissors/Ruler/Ball Point Pen
Test Procedure
Tensile Tester Settings

Set the tensile tester up as follows (These parameters are specific for TestWorks® software. If other control software is used the instructions should be modified as required by the specific software so as to achieve the same gage length, extension rate and data acquisition profile.):

| | |
|---|---|
| Test Speed | 100 mm/min |
| Gauge Length | 100 mm (see note) |
| Slack Compensation | 0.10N |
| Break Detection | 95% drop from Peak |
| Break Threshold | 0.25N (break detection remains inactive until this force is reached) |
| Data Acquisition Rate | 100 Hz |

Figure 2:
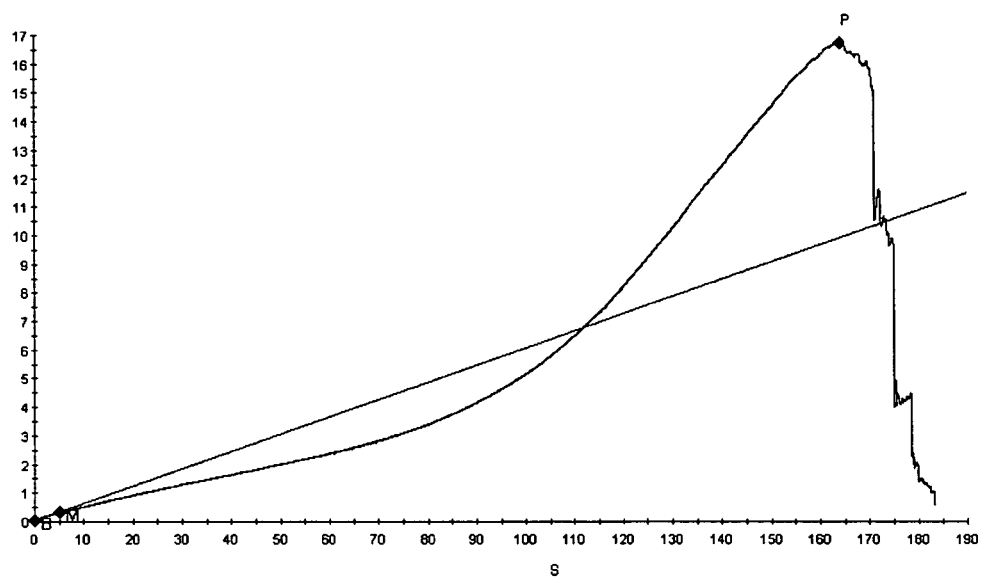
FIG. 2 is an exemplary force strain curve for a substrate material.

Measured Variables: Contemporary tensile testers also provide data acquisition and analysis software that is capable of providing the desired data outputs. FIG. 2 shows an exemplary load (L) stress (S) curve produced by a sample evaluated by this method. While such tensile testers can measure a full tensile property profile and both MD and CD samples can be analyzed, two variables are of interest with respect to the present invention.
1. Tensile Strength—Maximum Peak Force (Point P on FIG. 2) in Newtons to 1 decimal place.
2. Modulus—For purposes of this method, modulus is defined as the slope of the line intersecting the curve at 0.1% (FIG. 2 point B) and 5.0% strain (FIG. 2 point M), reported in N/m to 1 decimal place. Both of the strain points used to determine modulus should follow any inertial effects due to initial acceleration of the grips and fixtures to test speed.

Sample Preparation

1. Sample Conditioning: All samples (except wet, finished product) should be stored at 23±1° C. and 50±2% RH for at least 24 hours prior to testing.
2. Sample Preparation: All samples ($CD_1$ and MD) are to be cut using a precision 50 mm cutter and cut to a length of at least 150 mm (the sample should be gripped by at least 25 mm at each end). Check samples to insure they have been cut cleanly by the sample cutter.
   a. Nonwoven Substrate (Dry Raw Material): Cut at least n=10 specimens for. Samples should be allowed to equilibrate for at least 24 hours.
   b. Wet wipes: 3 containers should be tested. From each container, 4 samples should be taken from the top of the wipes stack, 4 from the middle and 4 from the bottom (total of 12 wipes/container). Samples should be cut from the center of each wipe.

Note: When cutting samples from wet, finished product, they must be kept at the same saturation levels as the other, uncut samples in the package. This can be accomplished by immediately returning the prepared samples to the opened package and that package sealed in a plastic bag until testing. Wet, finished product samples should be tested as soon as possible.

Execution

1. Make sure that the gauge length that is used is properly entered into the software system controlling the tensile tester. Start the tensile tester and pull the sample until break.
2. Insert a properly prepared sample into the jaws of the tensile tester and close the grip jaws to hold it in place.
3. Start operation of the crosshead using the machine control software.
4. Repeat steps 2 and 3 for all samples.
5. Discard the results of any sample where the sample slips during the test. Also, if the sample has excessive slack, and noise during the beginning of the test causes a 0.1N peak at the beginning of the test (inactivating slack compensation), calculated values may be incorrect. The 0.1N slack point should occur just prior to the force curve. Results of an evaluation of such samples should be discarded from the data and an additional sample evaluated Calculation/Reporting 1. Record and report the MD and CD Modulus and Tensile Strength for each replicate (see FIG. 2):
2. Repeat Step 1 for each specimen in the sample set.
3. Calculate and report the mean and standard deviation for each measured quantity.
4. Record the number of replicates used for testing.

Percent Bond Area

1. Obtain a full scale and dimensionally accurate print of the full pattern repeat which has the embossments shown in black and the non-embossments shown in white. This can be done in any known method, including printing out a to-scale pattern in black ink on white paper.
2. The total area of the pattern repeat is determined by measuring a known geometric shape, such as a square, rectangle, rhombus, etc. that encompasses all of the pattern repeat.
3. The total embossed area of the pattern repeat is measured by determining the area defined by all black regions within the pattern repeat. This can be done by scanning the pattern into a computer graphic file and using computer software such as Image 1.44 for Macintosh PC, PC Paint, Micrographics Designer, Adobe Illustrator, to determine the area of the black pixels within the geometric region established in Step 2 above. Alternatively, the total embossed area can be determined manually by superimposing a geometric grid consisting of 0.76 mm by 0.0.76 mm squares can on the geometric region established in Step 2. In this case the total embossed area is the total area of squares that are at least 50% black.
4. The percent bond area equals the ratio of the total embossed area and total pattern repeat area times 100.

EXAMPLES

Example 1

This example is intended to demonstrate the effect of a decorative emboss pattern of the prior art and an emboss pattern of the present invention on the mechanical properties of a wet wipe.

A spunlaced nonwoven material comprising a blend of 60% 1.5 denier polypropylene fibers and 40% 1.5 denier viscose fibers was obtained from Jacob Holm of Soultz, France. The material was slit into 279 mm wide rolls and run through a thermal embossing calender at 30.5 meters per minute for calender embossing. The calender comprised a roll pair with an engraved roll on top, the engraved roll being provided with either a decorative pattern of butterflies and hearts according to U.S. Pat. No. 6,361,784 or with a diamond pattern of closely spaced embossments as shown on wipe 10 in FIG. 1 (The embossments are disposed on the substrate along a series of parallel lines approximately 6 mm apart at an angle of about 45° from the machine direction in each direction so as to create a diamond shaped pattern on the substrate. The embossments are disposed at an embossment density of about 8 embossments/cm to so as to provide an embossed area of about 20%. Each embossment has a bonding area of about 1.25 $mm^2$.), and a smooth steel anvil roll on the bottom. Both rolls were heated to 129° C. and the bottom anvil roll was loaded with an effective nip pressure of 27 kilograms per linear centimeter.

The material was cut into 18 cm×20 cm sheets.

Sheets of the embossed nonwoven material were saturated with each of the cleaning lotion compositions shown in Table 1 at a level of about 3.4 gram lotion/gram substrate to form individual wet wipes.

TABLE 1

| Ingredient | Comp. A Concentration (%) | Comp. B Concentration (%) |
|---|---|---|
| Water | QS | QS |
| Tween 20[1] | 0.08 | — |
| Dimethicone (50 cst) | 1.75 | — |
| Decyl glucoside | — | 0.05 |
| ABILCARE 85[2] | — | 0.45 |
| KELTROL[3] | — | 0.18 |
| Stabylen-30[4] | 0.19 | — |
| Disodium EDTA | 0.1 | 0.1 |
| Citric Acid | — | 0.05 |
| Preservative System | 1.95 | 0.659 |
| Sodium Hydroxide | 0.14 | — |
| Perfume | 0.09 | 0.03 |

[1]Polysorbate 20 available from Uniqema of New Castle, DE
[2]85:15 bis-PEG/PPG-16/16 PEG/PPG-16/16 Dimethicone:capric-caprylic triglyceride from Degussa Care Specialties of Hopewell, VA
[3]Xanthan gum available from CP Kelco US of Wilmington, DE
[4]Acrylate/vinyl isodecanoate crosspolymer available from 3 V Inc. of Weehawken, NJ.

Lotion was applied as follows:
1. Three sheets of dry substrate were stacked, weighed and immersed in the requisite amount of cleaning lotion (based on sheet weight).
2. A hand roller was used to evenly distribute the lotion throughout the sheets.
3. The saturated substrate samples were stored in a ZIPLOC bag until they were evaluated for mechanical properties in order to prevent drying and a 4.5 kg weight is placed on the closed bag (after air is expelled therefrom) to aid in ply-to-ply contact.
4. Steps 1 through 3 were repeated with additional groups of three sheets until sufficient substrate was treated for the testing described below, removing the weight and adding to the stack of treated substrates in the bag as more substrate sheets are treated.

The wet wipes were then evaluated for CD modulus and CD peak tensile strength according to the method described in the Test Methods section above. The results of this evaluation are presented in Table 2.

TABLE 2

| Emboss Pattern | Cleaning Lotion | Mean CD Modulus (Newtons/m) | Mean Peak CD Tensile Strength (Newtons) |
|---|---|---|---|
| Unembossed | A | 19.8 | 13.8 |
|  | B | 21.0 | 11.8 |
| Butterflies and Hearts | A | 22.8 | 12.0 |
|  | B | 21.8 | 10.3 |
| Diamond | A | 34.2 | 9.2 |
|  | B | 38.3 | 7.6 |

As can be seen, the diamond emboss pattern of the present invention has both a higher CD modulus (i.e., greater stiffness) and lower CD peak tensile strength.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While various embodiments and/or individual features of the present invention have been illustrated and described, it would be obvious to those skilled in the art that various other changes and modifications can be made without departing from the spirit and scope of the invention. As will be also be apparent to the skilled practitioner, all combinations of the embodiments and features taught in the foregoing disclosure are possible and can result in preferred executions of the invention. It is therefore intended to cover in the appended claims all such changes and modifications that are within the scope of this invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wet wipe comprising:
    a) a cleaning lotion comprising an aqueous emulsion including an emollient and an emulsifier; and
    b) a nonwoven substrate comprising thermoplastic fibers and viscose fibers, said substrate having a basis weight less than about 55 grams/m$^2$ wherein said substrate is calender-embossed with embossments to form an emboss pattern, wherein said emboss pattern has a bond area greater than about 12% and less than about 25%, and wherein said embossments serve to join at least a portion of said thermoplastic fibers so as help provide said substrate with a wet CD modulus that is greater than about 25 N/m and less than about 70 N/m.

2. A wipe according to claim 1, wherein said nonwoven is spunlaced.

3. A wipe according to claim 1, wherein said substrate further comprises cellulosic fibers so as to form a fiber blend.

4. A wipe according to claim 3, wherein said cellulosic fibers comprise rayon.

5. A wipe according to claim 3, wherein said fiber blend comprises from 5% to 50% rayon, with the remainder of the fiber content being said thermoplastic fibers.

6. A wipe according to claim 4, wherein said thermoplastic fibers comprise polyolefin material.

7. A wipe according to claim 5, wherein said polyolefin material is polypropylene.

8. A wipe according to claim 1, wherein said bond area is greater than about 15%.

9. A wipe according to claim 1, wherein said wet CD modulus is greater than about 27 N/m.

10. A wipe according to claim 9, wherein said wet CD modulus is greater than about 30 N/m.

11. A wipe according to claim 1, wherein said basis weight is less than about 53 g/m$^2$.

12. A wipe according to claim 11, wherein said basis weight is between about 48 and about 52 g/m$^2$.

13. A wet wipe comprising:
    a) a cleaning lotion comprising an aqueous emulsion including an emollient and an emulsifier; and
    b) a nonwoven substrate comprising thermoplastic fibers and viscose fibers, said substrate having a basis weight of less than about 55 grams/m$^2$ wherein said substrate is calender-embossed with embossments disposed along parallel lines to form a repeating emboss pattern of diamonds, wherein said emboss pattern has a bond area greater than about 12% and less than about 25%, and wherein said embossments serve to join at least a portion of said thermoplastic fibers so as help provide said substrate with a wet CD modulus that is greater than about 25 N/m and less than about 70 N/m.

14. A wipe according to claim 13, wherein said cleaning lotion has a surface tension less than about 40 dynes/cm.

* * * * *